United States Patent [19]

Vo-Dinh

[11] Patent Number: 5,318,751
[45] Date of Patent: Jun. 7, 1994

[54] ENHANCED PHOTO-ACTIVATED LUMINESCENCE FOR SCREENING POLYCHLOROBIPHENYLS (PCBS) AND OTHER RELATED CHLORINATED COMPOUNDS

[75] Inventor: Tuan Vo-Dinh, Knoxville, Tenn.

[73] Assignee: Martin Marietta Energy Systems, Inc., Oak Ridge, Tenn.

[21] Appl. No.: 109,759

[22] Filed: Aug. 20, 1993

Related U.S. Application Data

[62] Division of Ser. No. 937,685, Sep. 1, 1992, Pat. No. 5,272,089.

[51] Int. Cl.$^5$ .................. G01N 33/18; G01N 21/64
[52] U.S. Cl. .................. 422/82.08; 436/126; 436/165; 436/172
[58] Field of Search .................. 250/461.1; 436/126, 436/172, 165; 422/82.07, 82.08, 82.05, 900

[56] References Cited

U.S. PATENT DOCUMENTS

| | | | |
|---|---|---|---|
| 4,666,672 | 5/1987 | Miller et al. | 422/68 |
| 4,803,049 | 2/1989 | Hirschfield et al. | 422/58 |
| 4,960,711 | 10/1990 | Aoki et al. | 436/124 |
| 5,094,817 | 3/1992 | Aoki et al. | 422/68.1 |

*Primary Examiner*—James C. Housel
*Assistant Examiner*—N. Bhat
*Attorney, Agent, or Firm*—Edward A. Pennington; Joseph A. Marasco; Harold W. Adams

[57] ABSTRACT

The presence of polychlorinated biphenyls and other chlorinated compounds in a sample is determined by treating the sample with a photo-activator and then exposing the treated sample to a UV light source. The UV light produces a photo-product complex, which is subsequently excited with UV light to cause luminescence of the complex. The luminescence is detected and characteristics of the luminescence spectra are used to determine the presence of chlorinated compounds and also the quantity of the chlorine in the compounds

15 Claims, 10 Drawing Sheets

ENHANCED PHOTO-ACTIVATED LUMINESCENCE FOR SCREENING POLYCHLOROBIPHENYLS (PCBS) AND OTHER RELATED CHLORINATED COMPOUNDS

This invention was made with Government support under contract DE-AC05-84OR21400 awarded by the U.S. Department of Energy to Martin Marietta Energy Systems, Inc. and the Government has certain rights in this invention.

This is a divisional of co-pending application Ser. No. 07/937,685 filed Sep. 1, 1992, now U.S. Pat. No. 5,272,089.

FIELD OF THE INVENTION

The present invention relates generally to the screening of polychlorinated biphenyls (PCBs) and other related chlorinated compounds and, more specifically, to an enhanced photo-activated luminescence apparatus and method for screening PCBs and related chlorinated compounds.

BACKGROUND OF THE INVENTION

Some chlorinated compounds, and in particular polychlorinated biphenyls (PCBs), have become a difficult environmental problem in that extremely minute levels are believed to present a health risk. PCBs are a class of 209 discrete chemical compounds known as "congeners", in which one to ten chlorine atoms are attached to biphenyl. PCBs were widely used for several decades due to their superior properties of chemical and physical stability, heat resistance and high electrical resistance. They were used in heat transfer systems, hydraulics/lubricants, transformers, capacitors, plasticizer applications and petroleum additives, just to name a few.

The chemical and physical stability, viewed once as an asset of the PCB, is now recognized as an environmental liability since the PCBs do not readily degrade after disposal. Now the use of PCBs is regulated in the United States under the Toxic Substances Control Act (TSCA), PL 94-469 (U.S. Congress, 1976). This law is administered by the United States Environmental Protection Agency (EPA). Various rules and regulations have been promulgated concerning the production, use and disposal of PCBs. Other countries have passed similar legislation, making the control of PCB use and disposal a world-wide concern. While PCBs are presently not in wide scale production, it has been estimated that up to 1.3 billion pounds were produced world wide through the year 1976.

Given the chemical and physical stability of PCBs, it has been of increasing concern to regulators to monitor and screen samples of various types for PCB contamination. In general, while the specifics of the various national laws may differ, there is a common interest in determining the presence of PCBs in the environment. Determination techniques used in the past include gas chromatography, thin-layer chromatography, and high-performance liquid chromatography. Non-chromatographic techniques include nuclear magnetic resonance (NMR) spectrometry, infrared (IR) spectrometry, and immuno-assays.

"Screening" techniques are determinations characterized by speed and/or simplicity of methodology and apparatus. Typically, samples are screened where immediate analysis is needed, such as analysis in the field or during an incinerator trial burn to make sure that the PCBs are being destroyed. In general, the analysis of PCBs generally requires selectivity and sensitivity. Even after cleanup of a PCB-contaminated site, PCBs are usually at ultra-trace levels in field samples, mixed with other halocarbons, lipids, etc. The levels of PCBs typically found in water, soil, tissue, food, biota and other matrices of interest are in the parts per billion (ppb) range. Most current measurement techniques for PCBs require the aforementioned chromatographic separation techniques, which are not practical for routine analysis in the field. A review of the state of the art in PCB detection can be found in *Analytical Chemistry of PCBs* by M.D. Erickson (Butterworth Publishers, 1986). As described therein, packed column gas chromatography (GC), thin-layer chromatography (TLC), and high-performance liquid chromatography (HPLC) have been used to provide data on total PCB contents in samples. Packed column GC/ECD is the common method for quantification of PCBs such as AROCLORS made by the Monsanto Corporation in the American National Standards Institute (ANSI) procedures. In this procedure, the PCBs are quantified against an AROCLOR standard using the largest peak, or a secondary peak if necessary. Typically, this procedure was used to determine PCBs in sediments and soils.

If congener-specific determination is required, high-resolution gas chromatography (HRGC), which uses fused silica capillary columns, would be the preferred technique. High-resolution gas chromatography has been used for the analysis of PCBs in transformer fluids or waste oils.

Various mass spectrometry (MS) techniques, including electron impact MS, chemical ionization MS, coupled MS/MS, etc., have been used to analyze complex PCB samples. Methods involving perchlorination of the biphenyl ring of the PCB congeners have been used in the determination of PCBs. One limitation of the perchlorination approach is due to the fact that biphenyl can also be perchlorinated, thus leading to erroneously high blank levels.

Thin-layer chromatography (TLC) has been used in the analysis of PCBs. Detection using this technique has involved spraying the plates with silver nitrate followed by UV irradiation and fluorescence. See R.H. DeVos and E.W. Peet, *Bul. Envir. Contam. Toxicol.*, 6 (2), 164, 1971, for UV irradiation and J. Stahr, *Liq. Chromatogr.*, 7, 1393, 1984, for fluorescence. Two dimensional TLC has been used for PCB analysis, as described by N.V. Fehringer and J.E. Westfall in *J. Chromatogr.*, 57, 397, 1971. Photo-degradation of PCBs is a previously known process and fluorescence following UV excitation has been reported. See *The Chemistry of PCBs* by O. Hutzinger et al., R.E. Krieger Publishing Co., 1983.

Sensitized room temperature phosphorescence (RTP) has been used as the detection method for HPLC in PCB analysis. The method is based on the transfer of triplet energy of the analyte molecule (donor) to biacetyl (acceptor) and detection of sensitized RTP of biacetyl in liquid solutions. See T. Vo-Dinh, *Room Temperature Phosphorimetry For Chemical Analysis*, Wiley Publishers, 1984. The RTP method has recently been applied to PCB analysis.

In spite of the myriad techniques available in the prior art, a strong need still exists to have a rapid and simple technique to screen for PCBs under field conditions.

SUMMARY OF THE INVENTION

An object of the present invention is to provide a method and apparatus for testing samples for PCBs and related chlorinated compounds which is quick and relatively simple, thus facilitating field screening analysis to allow rapid decisions in a clean-up operation and avoid the need for return visits to a site by a cleanup crew.

Another object of the present invention is to provide a method and apparatus which are capable of making determinations of PCBs and chlorinated compounds in field samples without having to use extensive and costly laboratory analyses of samples.

Another object of the present invention is to provide a method and apparatus for testing samples for chlorinated compounds which can permit screening of samples at a low per-analysis costs.

These and other objects of the invention are met by providing an apparatus for testing a sample for PCBs and related chlorinated compounds which includes a photo-activator applied to the sample to form a complex of the photo-activator and chlorinated compounds if present in the sample, first U.V. light source means for activating the photo-activator to form a luminescent photo-product complex, second light source means of sufficient energy for exciting the photo-product complex to a luminescent state, and means, in proximity to the sample, for detecting the luminescence of the photo-product complex. Preferably, the luminescence has a band and maximum peak, the maximum peak being indicative of the presence of chlorinated compounds in the sample. The first and second light source means may comprise a single light generator and two optical filters for producing U.V. light or near U.V. light first for photo-activation and then excitation. Alternatively, two different U.V. light sources may be employed. While the light sources are preferably emitting U.V. light, a visible light laser could also be used with two-photon or multiple-photon excitation so that the emitted radiation is in the U.V. range or slightly above.

Other objects, advantages and salient features of the invention will become apparent from the following detailed description, which, taken in conjunction with the annexed drawings, discloses preferred embodiments of the invention.

DETAILED DESCRIPTION OF THE PREFERRED EMBODIMENTS

Figure 1:
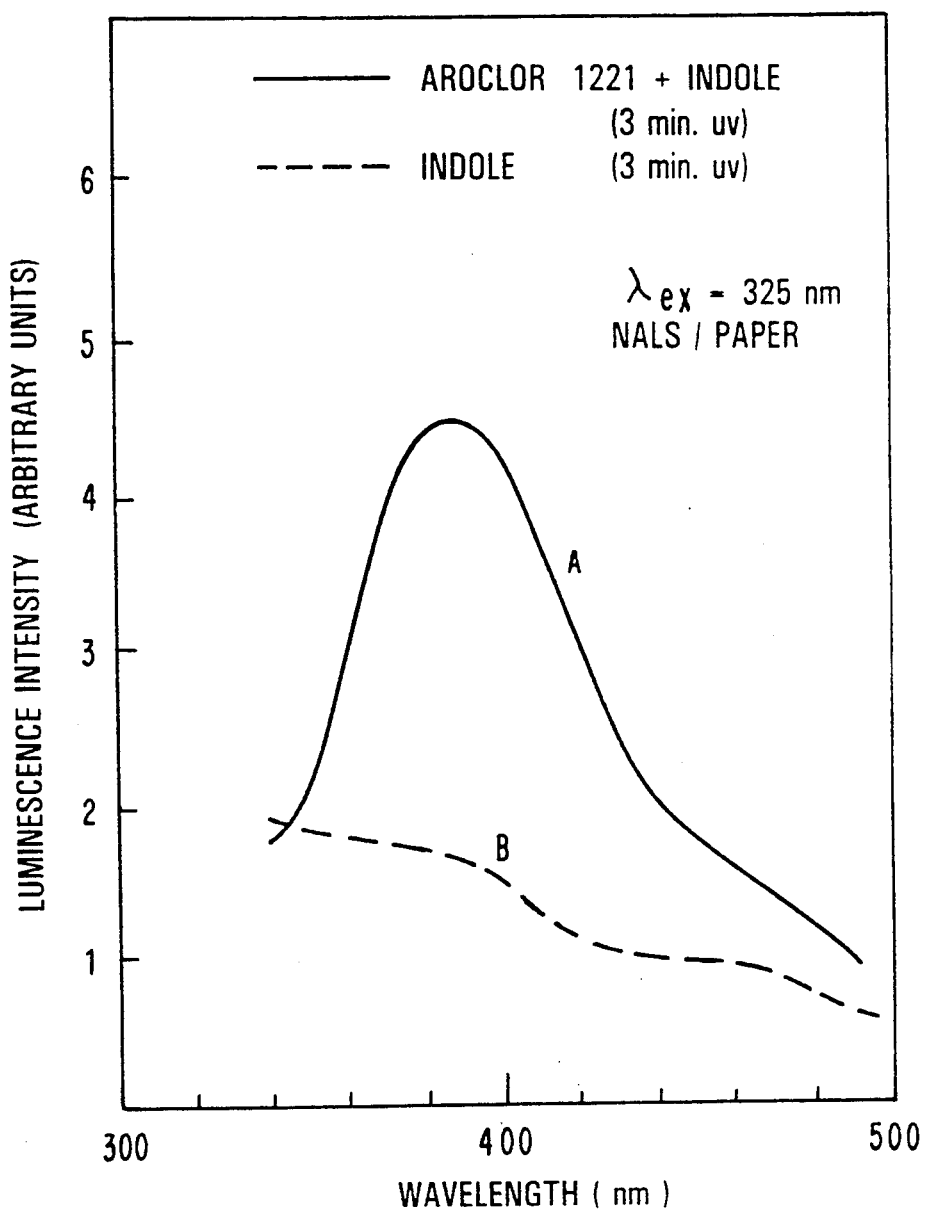
FIG. 1 is a graph showing luminescence spectra of indole/PCB (Aroclor 1221) photo-product as curve "A", and of idole alone as curve "B", using a 325-nm excitation source following 3 minute photo-activation at 254 nm.

The present invention is based primarily on a three-step procedure which combines several processes that are integrated to provide a relatively simple and inexpensive screening of chlorinated compounds such as PCBs.

As a first step, a sample which is to be tested or screened for the presence of chlorinated compounds such as PCBs is treated with a photo-activator. Suitable photo-activators include indole, diphenylamine (DPA), pyrrole, and imidazole. The photo-activator and PCBs present in the sample form a complex. The present invention encompasses the discovery that in the presence of a suitable photo-activator, illumination of PCBs with ultraviolet (UV) light (at wavelength $\lambda_1$) results in the generation of a luminescent photo-product of the photo-activator/PCB complex. The photo-product complex is then excited with a light source at a different wavelength ($\lambda_2$) than the first illumination. The luminescence product of the second illumination step is detected at still another excitation wavelength ($\lambda_3$), $\lambda_3$ being $>\lambda_2$. In general, $\lambda_3>\lambda_2$. There is no specific relationship between $\lambda_1$ and $\lambda_2$, although experiential data shows that $\lambda_2>\lambda_1$. $\lambda_1$ is UV light of sufficient energy to form the photo-product, and $\lambda_2$ is UV light of sufficient energy to excite the photo-product into an excited electronic state leading to subsequent fluorescence at $\lambda_3$.

A possible process in photo-chemical reaction is reductive dechlorination of the PCBs which involves C—Cl bond cleavage to produce biphenyl free radical species. Formation of a luminescent product is likely due to interaction of the biphenyl free radical species and/or of the chlorine ions (photolyzed from PCB under UV irradiation) with the photo-activator. Since Aroclors are complex mixtures of PCBs, the exact photo-chemical reactions and kinetics for each congener cannot be described in detail.

Photo-chemical degradation of PCBs via UV irradiation is determined by the degree of chlorination and the positions of chlorine substitution in the biphenyl nucleus. This photochemical reaction involving the photo-activator increases with time as indicated by the increase in luminescence intensity, which reaches a maximum within 3–7 minutes (depending on the type of Aroclor).

The following reaction mechanisms may be involved for a complex of PCB and either indole or DPA:

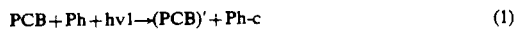

$$PCB + Ph + h\nu_1 \rightarrow (PCB)' + Ph\text{-}c \qquad (1)$$

$$Ph\text{-}c + hv2 \rightarrow (Ph\text{-}c)^* \quad (2)$$

$$(Ph\text{-}c)^* \rightarrow Ph\text{-}c + hv3 \quad (3)$$

where:
hv1 = UV irradiation for photo-activation (e.g. 254 nm)
hv2 = excitation of the complex Ph-c (e.g. 325 or 354 nm)
hv3 = luminescence from the excited state (Ph-c)* (405 nm)
(PCB)' photo-product of PCB following UV irradiation with hv1
Ph = photo-activator (e.g., indole, DPA)
Ph-c = ground state of photo-activator product complex following interaction with PCB and hv1 irradiation
(Ph-c)* = excited electronic state of Ph-c In the above, step (1) is the photo-activation step, step (2) is the excitation of the photo-product step, and step (3) is the detection of luminescence step. The luminescence from (Ph-c)* appeared during experimentation to be fluorescence (from an excited single state) since the emission decay time was very fast, although involvement of an excited triplet state process and/or phosphorescence emission should not be rules out and may occur under certain specific conditions.

EXAMPLE 1

Indole Photo-activator

Indole alone exhibits no luminescence when excitation is used at 325 nm since it absorbs at higher energies (i.e., shorter wavelengths). PCBs do not show luminescence under similar excitation conditions. However, when PCBs are in the presence of indole, UV irradiation of the mixture PCB/indole using 254 nm (hv1) light, a photo-product complex Ph-c is formed. When this photo-product complex Ph-c is excited by hv2 (e.g. 325 nm) excitation (step 2), a luminescence emission with a maximum peak at approximately 390 nm can be detected. It is noteworthy that UV irradiation of indole or PCBs separately do not produce the 390 nm luminescence. The luminescence of the photo-product illustrate in FIG. 1 can be used to identify and quantify PCBs.

FIG. 1 represents a luminescence spectra generated for a PCB Aroclor 1221 + indole, which was initially excited with a UV light source at an excitation wavelength of 254 nm, followed by a second excitation at an excitation wavelength ($\lambda ex$) of = 325 nm for 3 minutes. The sample containing Aroclor 1221 and indole was placed on a paper substrate treated with sodium lauryl sulphate (NaLS). The graph of FIG. 1 was produced by an X-Y plotter of an analog recording system of a luminescence spectrometer. The spectrometer will be described in more detail below. Graph "A" shows luminescence of the indole/PCB photo-product, while graph "B" shows luminescence of only indole.

EXAMPLE 2

DPA Photo-activator

Figure 2:
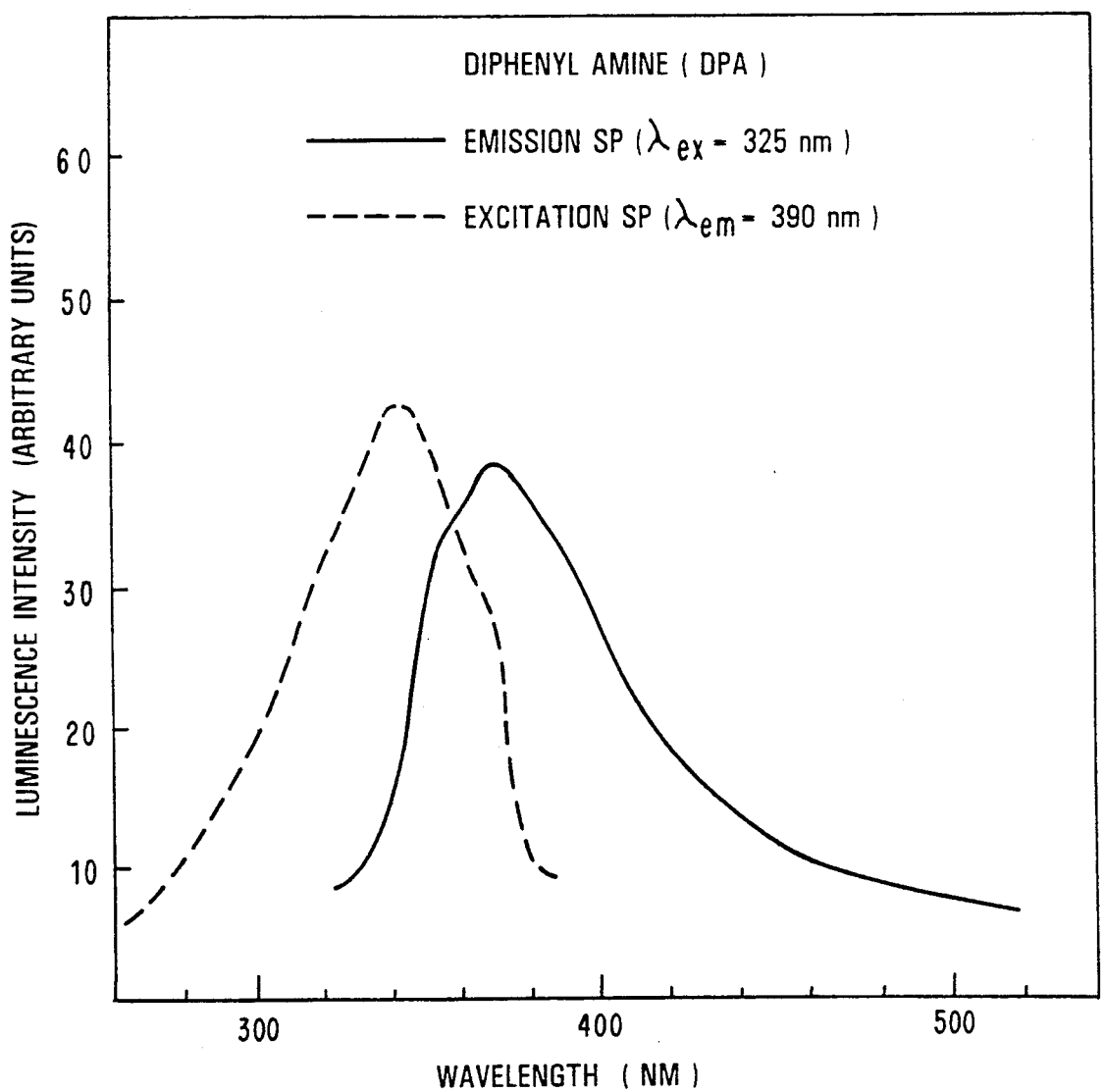
FIG. 2 is a graph showing luminescence spectra of diphenylamine (DPA)

As shown in FIG. 2, the photo-activator DPA exhibits luminescence having a maximum peak at approximately 365 nm. Following UV irradiation (hv1) of the mixture of PCB and DPA at 254 nm (hv1) with a handheld lamp (Model UVGL-58, UVP, Sam Gabriel, Calif.) the photo-product Ph-c is formed. This complex Ph-c exhibits a broad-band luminescence at approximately 405 nm, as seen in FIGS. 3)a) and (b), when it is subjected to hv2 excitation at <360 nm (e.g., 325 nm or 354 nm). The optimum UV irradiation (254 nm) time is 3-5 minutes. The 254 nm line of the handheld lamp was used because of its availability and this excitation wavelength can photo-induce PCBs, which have absorption up to 280 nm. Use of another wavelength (e.g., <254 nm) is also possible as long as it is capable to photo-activate the PCB-DPA complex.

Figure 3A:
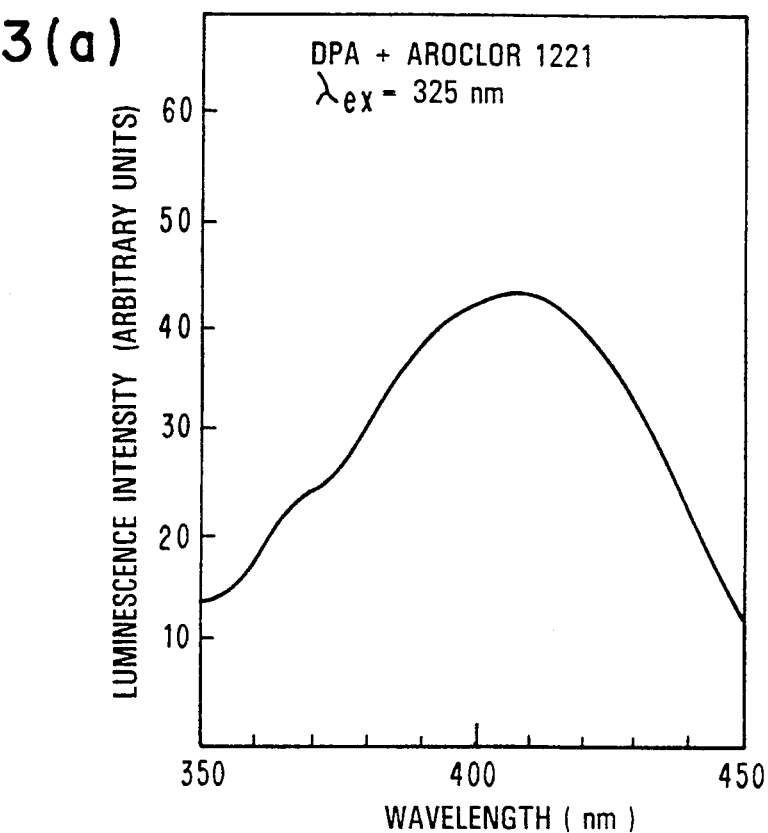
FIGS. 3(a) and 3(b) are graphs showing luminescence spectra of DPA and PCB complexes, with excitation at 325 nm and 355 nm, respectively.
Figure 3B:
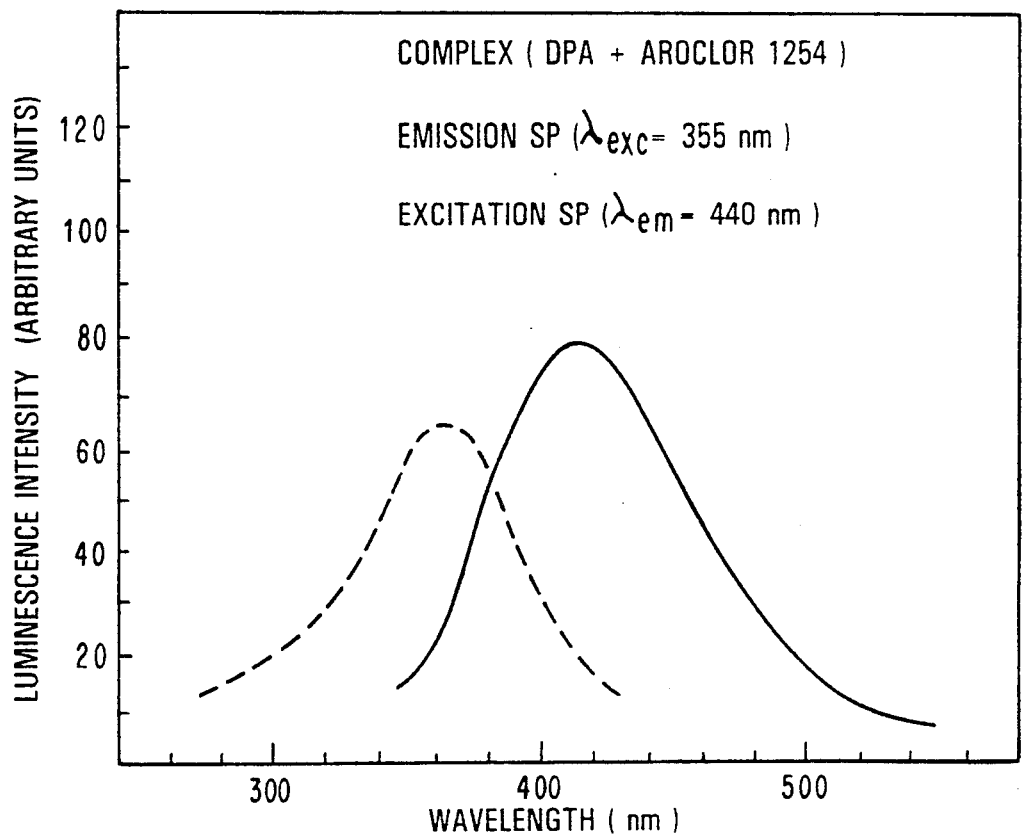

For a sample containing only DPA and no PCB, a strong emission peak at 365 nm was generated, as seen in FIG. 2. This emission peak is associated with DPA luminescence. When PCB is added to DPA and the resulting mixture is subjected to 254 nm UV irradiation, the luminescence peak of DPA at 365 nm decreases whereas a new luminescence emission band at 405 nm (hv3) appears. The 405 nm luminescence band is associated with the photo-product complex DPA-c since it is proportional to the amount of PCB added to the DpA sample. As shown in FIGS. 3(a) and 3(b), a decrease of the 365 nm band (associated with DPA luminescence) with a simultaneous increase of the 405 nm emission (associated with the complex DPA-c) manifests the presence of PCB.

If the excitation occurs at 354 nm instead of 325 nm, the emission band at 405 nm is observed with minimal interference from the 365 nm band. This is due to the fact that the 354 nm excitation masks the DPA emission at 365 nm. This is also due to the fact that DPA is not excited or weakly excited by the 354 nm excitation light.

In the foregoing examples, DPA and indole were used to illustrate the capability of the present invention to detect the presence of PCBs in samples. It is also possible to determine the chlorine content of the PCB mixture contained in the sample. According to the present invention, the luminescence intensity at, for example, hv3 = 405 nm, is due to the reaction PCB/hv1/DPA. This intensity has been found to be proportional to the number of total chlorine in the PCBs. This is consistent with the photo-chemical dechlorination of PCBs. To demonstrate, an example is given below involving a given PCB sample with a number "n" proportional to the total of chlorine content. This feature confirms that the photo-chemical reaction involves dechlorination PCBs:

$$PCB \text{ (with n Cl atoms)} + n \ hv1 \rightarrow PCB' + n \ Cl \quad (4)$$

$$n \ Cl + n \ DPA \rightarrow n \ (DPA\text{-}c) \quad (5)$$

$$n \ (DPA\text{-}c) + n \ hv2 \rightarrow n \ (DPA\text{-}c)^* \quad (6)$$

$$n \ (DPA\text{-}c)^* \rightarrow n \ (DPA\text{-}c) + n \ hv3 \text{ (luminescence)} \quad (7)$$

Equation 7 above indicates that the luminescence intensity (hv3) is proportional to n, the number of total chlorine atoms in PCB samples. For example, with Aroclor 1221, n=21; with Aroclor 1254, n=54; with Aroclor 1260, n=60, etc. With a sample containing varying amounts of different Aroclors, e.g., 10% Aroclor 1221, 60% Aroclor 1254, and 30% Aroclor 1260, the number n is equal to 2.1 (10% of 21) + 32.4 (60% of 54) + 18 (30% of 60) = 52.5. It is therefore possible to quantify the total chlorine content of a complex sample having different amounts of Aroclors by measuring the intensity of the emission band at 405 nm. The quantitative determination of total chlorine content of several mixtures of different Aroclors is shown in Table 1 as follows:

TABLE 1

QUANTITATIVE DETERMINATION OF TOTAL CHLORINE CONTENT IN COMPLEX MIXTURE OF PCB (AROCLOR)

| MIXTURE OF AROCLOR (*) | EXPERIMENTAL (% Cl Content) | THEORETICAL (% Cl) |
|---|---|---|
| With DPA as the Photo-Activator | | |
| 1262 (5 μL) + 1254 (3 μL) + 1242 (2 μL) | 52 | 54.6 |
| 1260 (6 μL) + 1248 (3 μL) + 1242 (1 μL) | 52 | 54.6 |
| 1254 (2 μL) + 1242 (3 μL) + 1248 (5 μL) | 43 | 47.4 |
| 1221 (3 μL) + 1242 (2 μL) | 30 | 29.4 |
| With Indole as the Photo-Activator | | |
| 1221 (6 μL) + 1232 (4 μL) | 28 | 25.4 |
| 1248 (2 μL) + 1260 (3 μL) + 1221 (5 μL) | 39 | 38.1 |

(*) Aroclor No. sample is designated by 4-digit number

TABLE 2

LIMIT OF OPTICAL DETECTION (LOD) USING THE PRESENT ENHANCE LUMINESCENCE TECHIQUE WITH NALS AND TiO2 TREATMENT

| ANALYTE | LOD (PART-PER-BILLION) |
|---|---|
| Aroclor 1121 | 4.2 |
| Aroclor 1242 | 2.3 |
| Aroclor 1248 | 2.3 |
| Aroclor 1254 | 2.5 |
| Aroclor 1260 | 3.0 |

Figure 4:
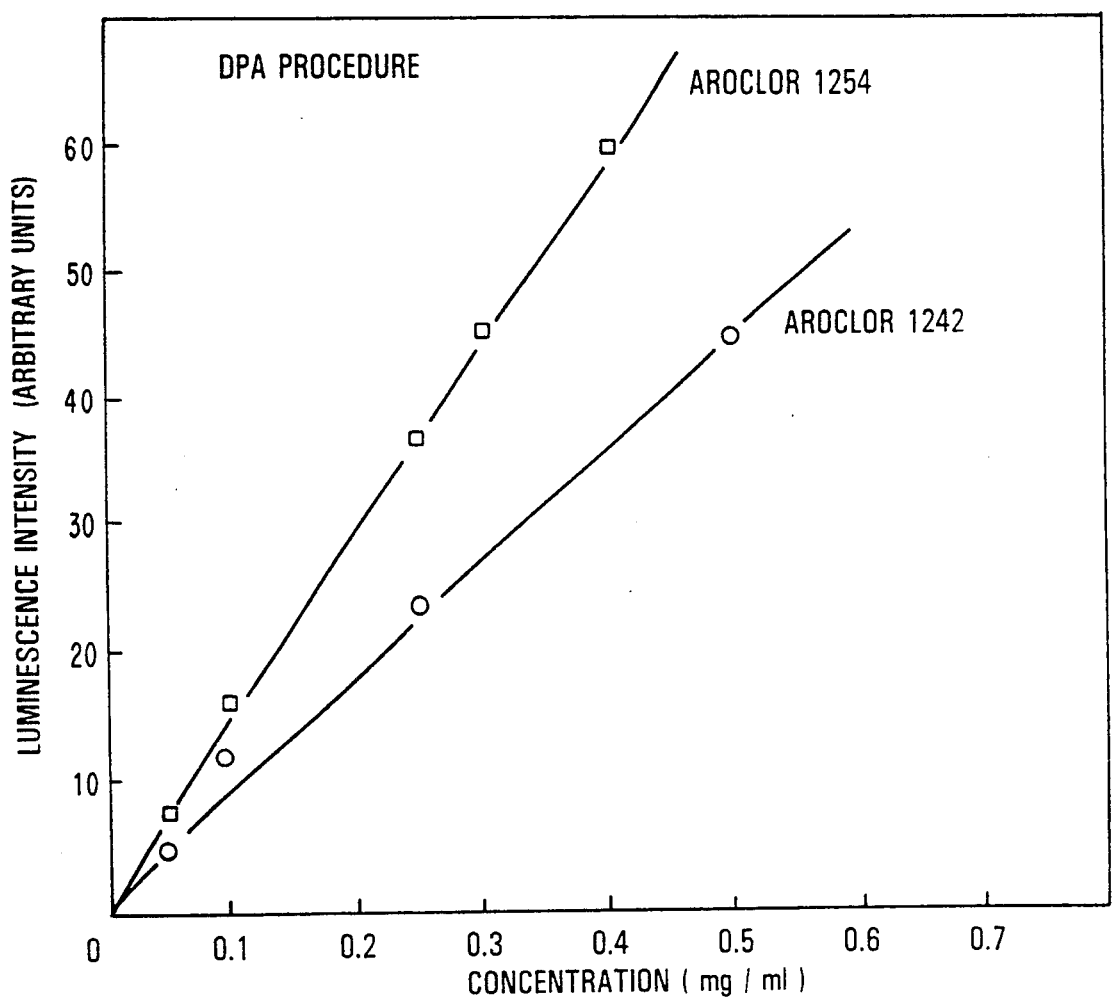
FIG. 4 is a graph showing calibration curves for Aroclor 1254 and Aroclor 1242.
Figure 5:
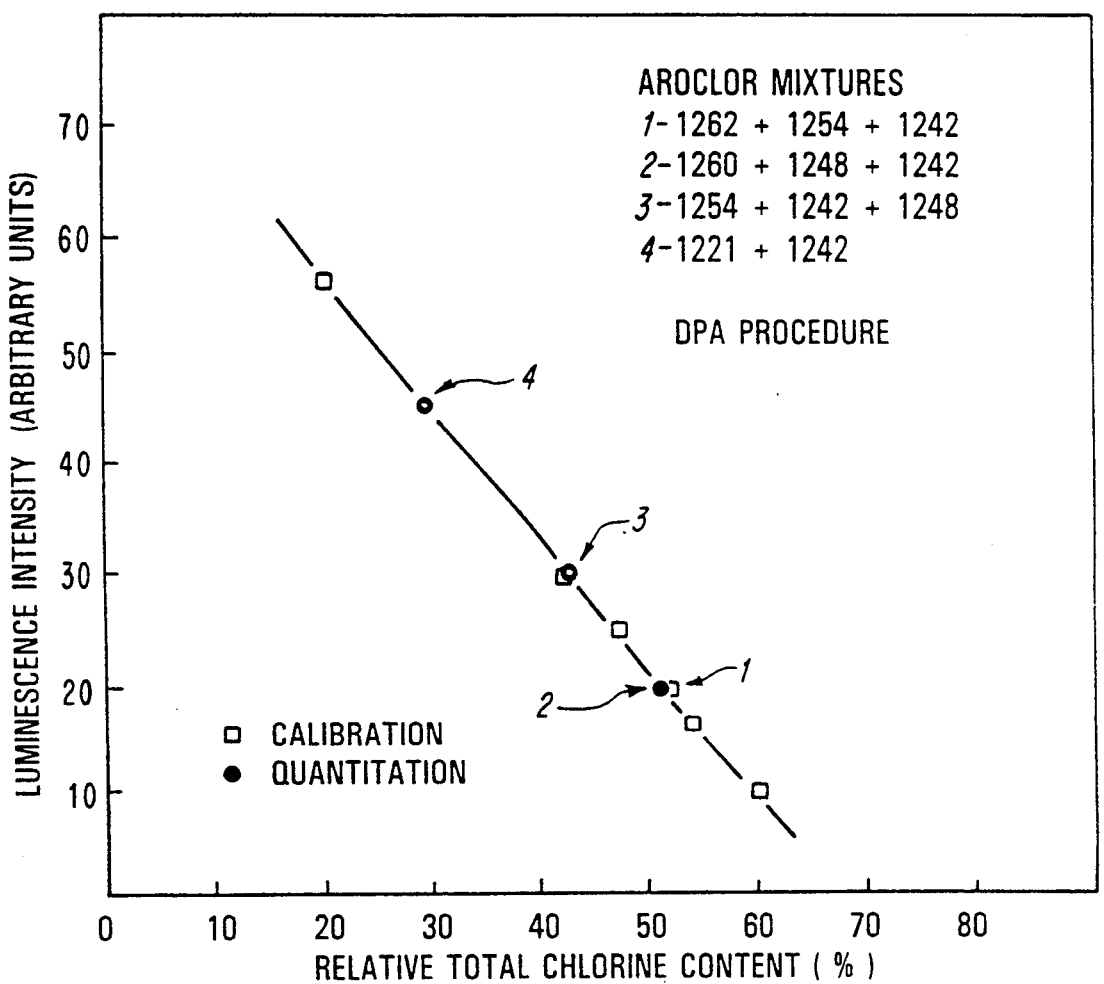
FIG. 5 is a graph showing the relationship between luminescence intensity and total chlorine content using the DPA photo-activation.
Figure 6:
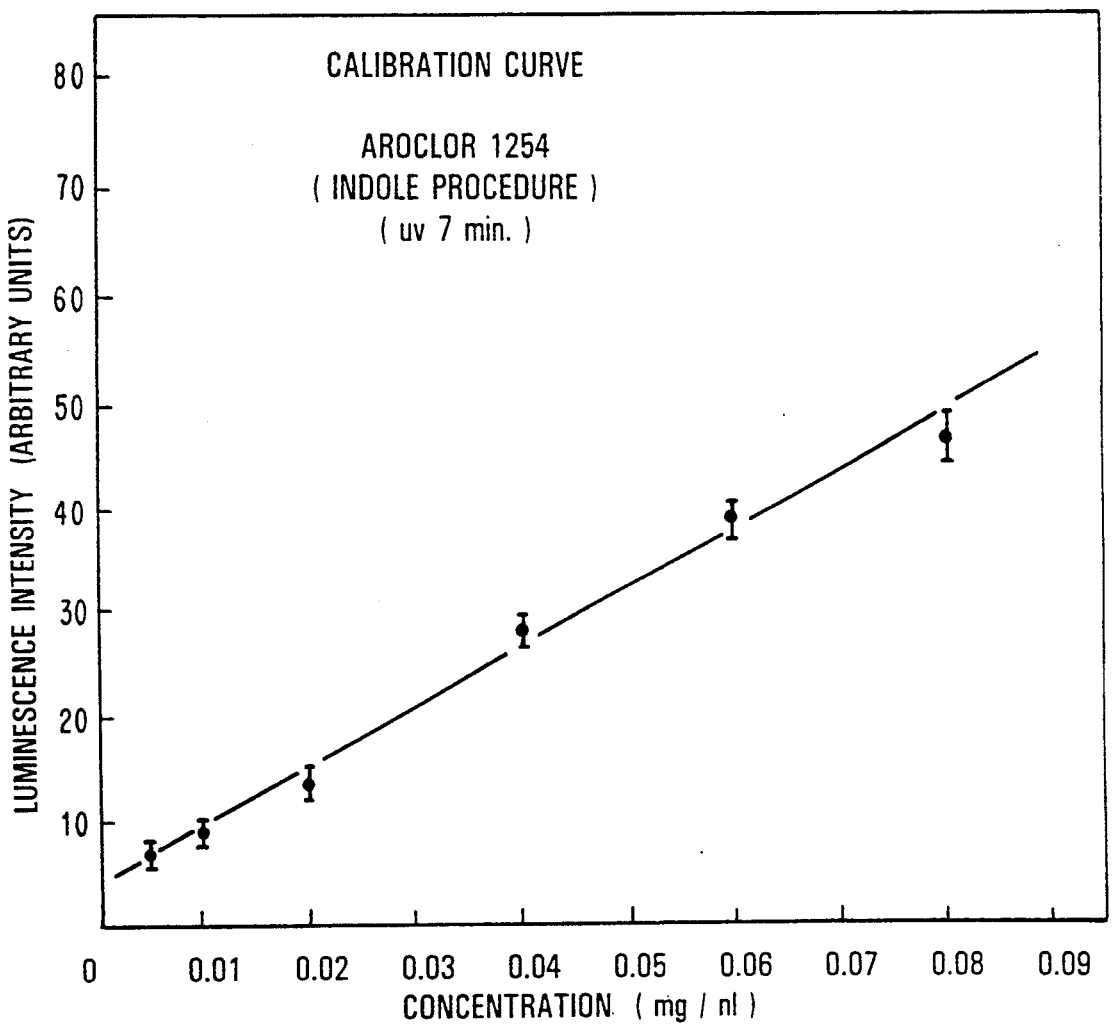
FIG. 6 is a graph of a calibration curve of the PCB Aroclor 1254 using the indole photo-activator.
Figure 7:
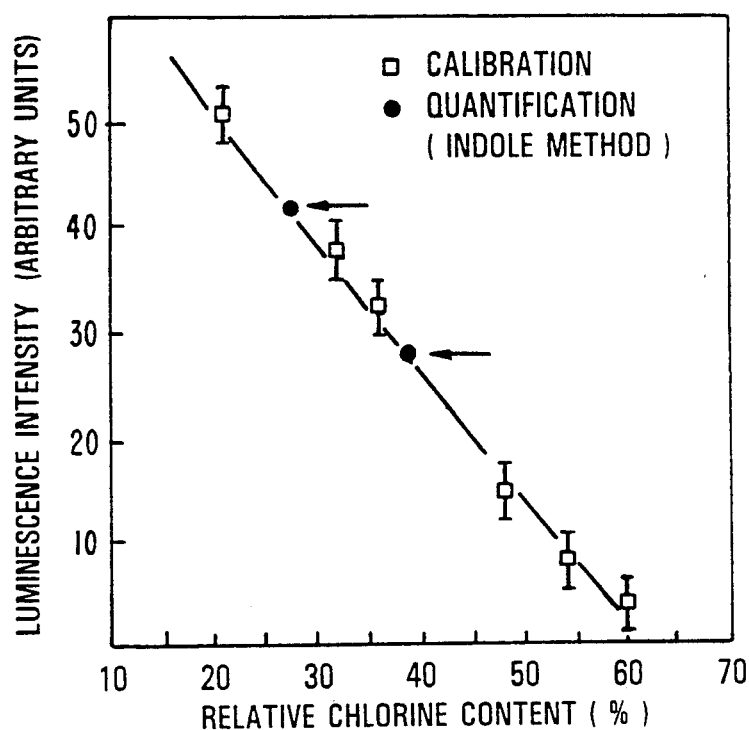
FIG. 7 is a graph used to determine chlorine content of a sample using the indole enhanced photo-activated luminescence technique of the present invention.

FIG. 4 shows examples of calibration curves for Aroclors 1242 and 1254. The limits of detection for Aroclors 1221, 1254, and 1260 are 4, 2.5, and 3 ppb, respectively. The relationship between luminescence intensity and the chlorine content of the complex mixtures is illustrated in FIG. 5. The total chlorine content of Aroclors discussed in Table 1 is determined with the quantitation data in FIG. 5. Similar results using indole as the photo-activator are illustrated in FIG. 6 (calibration curve of Aroclor 1254) and FIG. 7 (determination of chlorine content).

One aspect of the present invention is the treatment of the substrate to achieve an enhanced photo-activation and detection. This treatment was mentioned briefly above as a surfactant applied to the surface of the substrate. Without the substrate treatment procedures, the sensitivity and reproducibility may not be sufficient for quantitative determination of chlorine content of PCB. Two substrate treatment procedures, involving surfactants and $TiO_2$ semiconductor particles, are described below.

In one embodiment of the invention, the substrate is treated with sodium lauryl sulfate (NaLS). Other surfactants, such as CTAB, the nonionic surfactant ethylene oxide propylene oxide condensate Genpol-20, cyclodextrins, micellar systems, etc., could be used as well. In the surfactant media, the sensitivity, stability, and selectivity of photo-physical reactions are improved and photo-chemical products and complexes are generally more stable than when formed in the absence of surfactants. The presence of NaLS improves the efficiency of the photo-chemical interactions between PCB, S, and light. Surfactants have several unique properties which should facilitate analytical measurements using photo-luminescence. For example, they have the ability to solubilize and concentrate reactant (DPA/analyte) and they can alter quantum efficiencies, chemical and photo-physical pathways and rates. As a result of the surfactants, an increase in the luminescence intensity of each PCB test is expected and has been observed using NaLS. It is thus possible to lower the detection limits of the assay and achieve greater sensitivity. This is a particular advantage achieved by the present invention, given that PCBs need to be screened on a ppb basis. Additionally, surfactants are optically transparent, stable, photo-chemically inactive, inexpensive, and relatively nontoxic. The use of surfactants is an important step since it makes the luminescence technique of the present invention more sensitive and more reproducible, thus allowing quantification of the chlorine content. According to one particular embodiment of the present invention, the intensity of (ph-c)* is maximum for an NaLS concentration of 1% on the substrate.

The substrate may also be treated with the photo-activator, to form a complex with the sample placed on the substrate. Thus, the photo-activator can be either mixed into the sample or placed on (or in) the substrate, or both.

Figure 8:
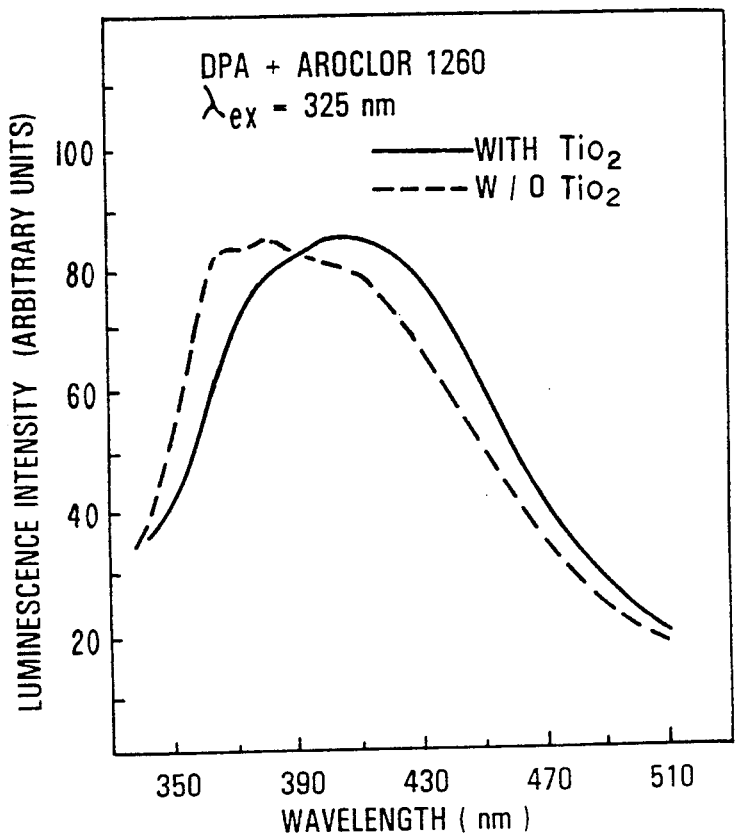
FIG. 8 is a graph showing luminescence spectra for a DPA and PCB complex with and without a treatment on the substrate using titanium oxide coating.

Another treatment of the substrate according to the present invention involves the use of semiconductor particles. Semiconductors, dispersed as colloids, powders, crystalline films, or single crystals, halve been effectively employed for driving charge separation processes, redox reactions of both organic and inorganic substrates. In the present invention, treating the substrate with can enhance the formation of the luminescent DPA-PCB complex. This might be due to an increase in the speed of the DPA-PCB complex formation in the presence of . FIG. 8 shows that with treatment the emission of DPA at 365 nm decreases whereas the emission at 405 nm (from DPA-c) increases, thus reflecting a more efficient formation of the DPA-c photoproduct of interest.

Figure 9:
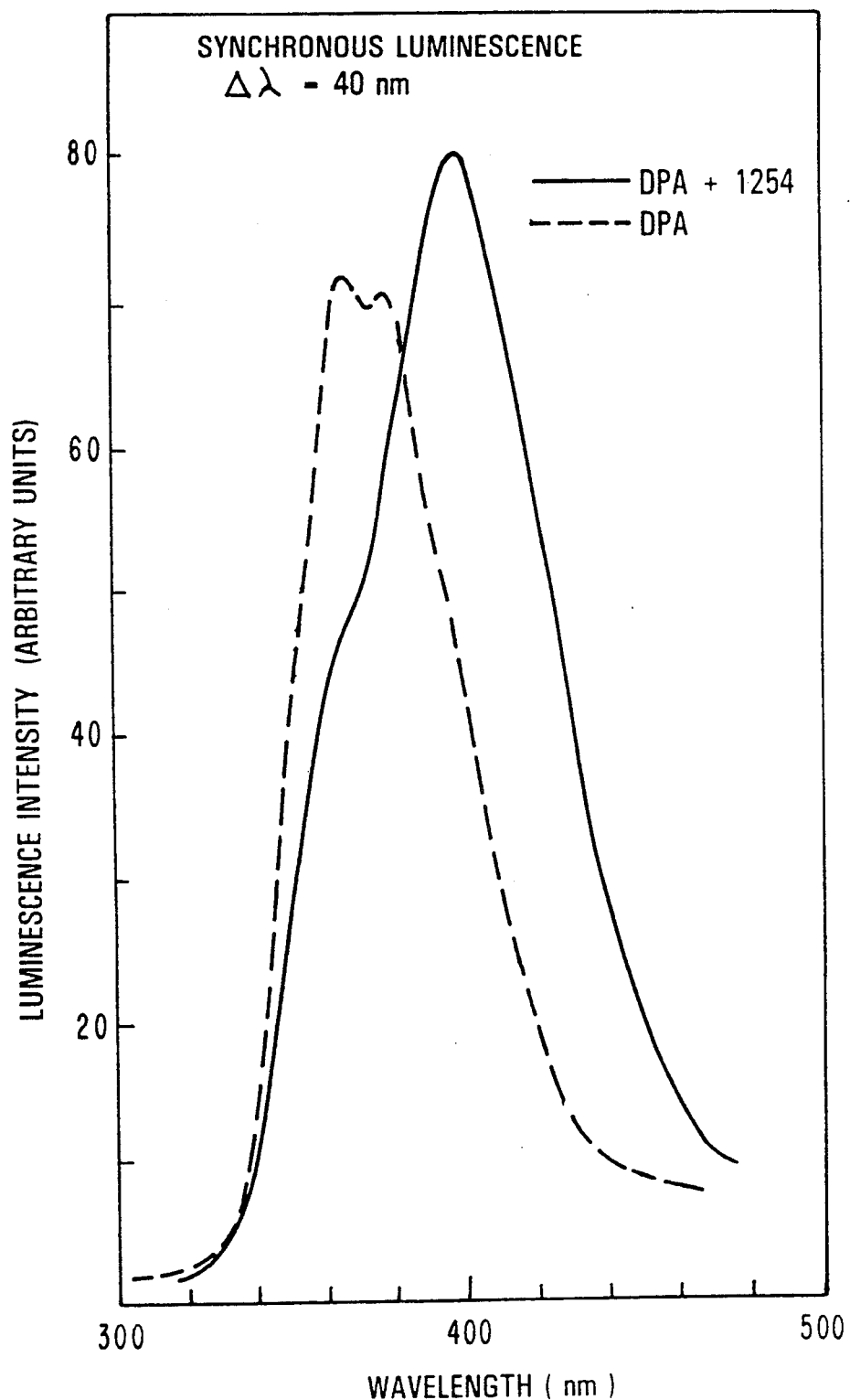
FIG. 9 is a graph showing synchronous luminescence spectra of DPA and DPA-c.

The selectivity of the present enhanced photo-activated luminescence technique can be further improved by using the synchronous excitation or synchronous luminescence (SL) method. The synchronous methodology consists of scanning both excitation and emission wavelengths simultaneously, by keeping a constant wavelength interval between them. The SL technique has been described by T. Vo-Dinh in *Modern Fluorescence Spectroscopy*, E.L. Wehry, Ed., Plenum Press, New York, 1981), which is incorporated herein by reference. FIG. 9 shows the SL spectra of DPA and DPA-c using a wavelength interval of 40 nm. The SL technique narrows the emission bands of DPA and DPA-c, thus permitting a better spectral separation of these two species when both are present.

Figure 10:
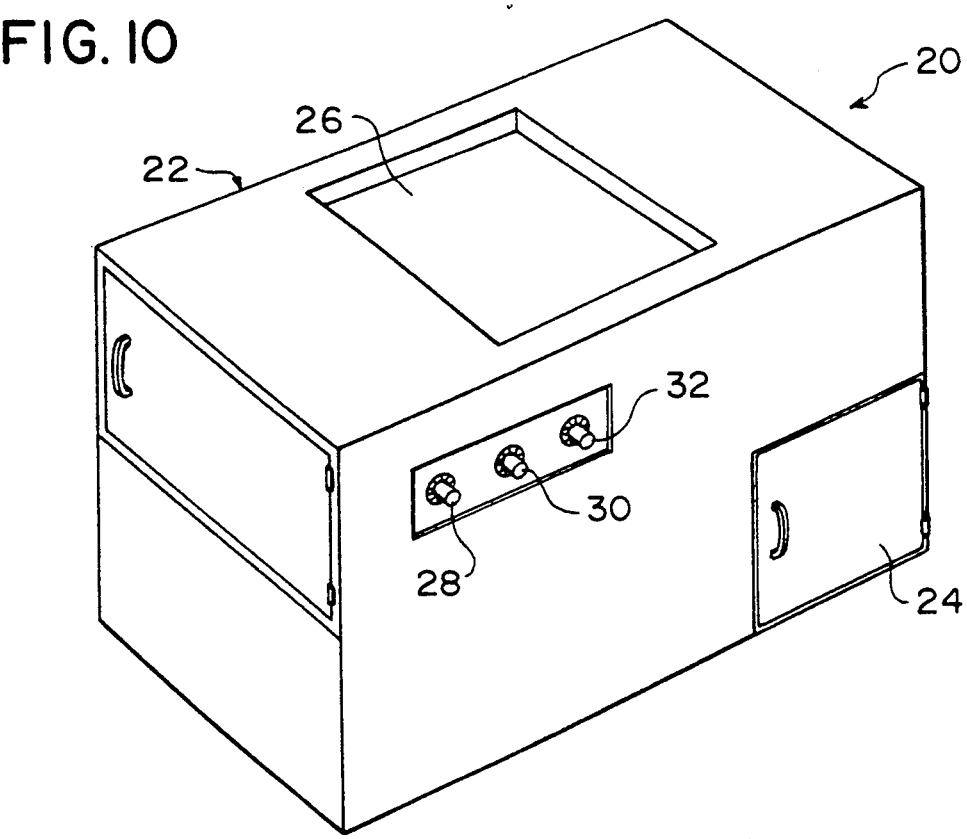
FIG. 10 is a perspective view of a portable field instrument for screening samples for PCBs and related chlorinated compounds according to the present invention.
Figure 11:
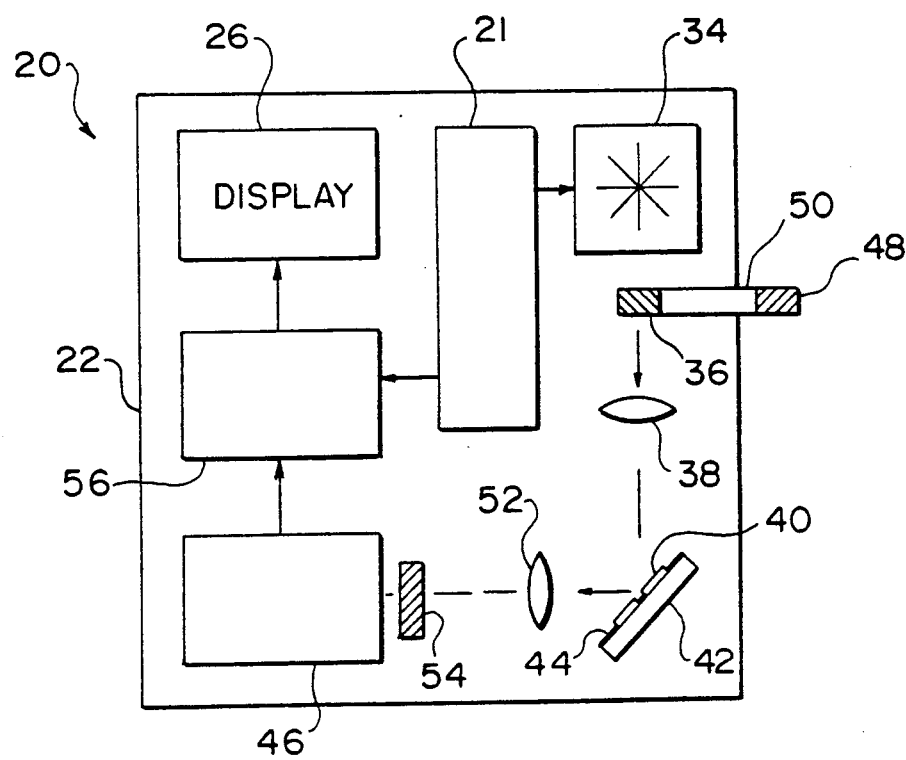
FIG. 11 is a schematic view of the portable field instrument of FIG. 10.

Due to the relative simplicity of the present technique, a portable field instrument can be used in which the entire sampling/irradiation/detection protocol for the inventive technique are integrated. Referring to FIGS. 10 and 11, a portable field instrument 20 for testing samples for chlorinated compounds such as PCBs includes a housing 22 having an overall size and shape suitable for carrying in an instrument carrying case (not shown). The housing 22 has a sample door 24 which can be opened to gain access to a sample holder (not shown in FIG. 10). The field instrument 20 includes a digital display 26 or other suitable indicator means so that when the technician makes a field analysis of a sample of material potentially containing PCBs, for example, the results of the analysis can be viewed immediately.

Preferably, the instrument 20 has a self-contained battery power supply 21 so as to facilitate remote-site screening. A power on/off switch 28, a timer dial 30, and a light source wavelength selector 32 are provided on the housing 22 for easy access by the technician. The timer dial switch 30 can be programmed to select, adjust, and synchronize the photo-activation time, excitation time, and detection time automatically.

Referring to FIG. 11, a UV light source 34 disposed within the housing 22 radiates light at a wavelength determined by an optical filter 36. The optical filter 36 provides that the light passing therethrough is at the desired, predetermined wavelength. In the examples described above, this would correspond to hv1 or 254 nm so as to provide the necessary photo-activation of the PCB/photo-activator. A lens 38 focuses the UV light onto the sample 40 which is mounted on a sample holder 42. A paper sheet 44 mounted on the sample holder 42 is preferably treated with a surfactant as described above to enhance the sensitivity of the screening technique.

Irradiating UV light at 254 nm on the sample 40 for a predetermined period of time forms a photo-product complex from a mixture of PCB and photo-activator, such as indole, contained in the sample 40. The photo-product complex is then excited by UV light at another wavelength of, for example, 325 nm. This causes a luminescence emission with a maximum peak at approximately 390 nm which is detected by a photo-detector 46. In order to produce excitation at the second wavelength, the first optical filter 36 is replaced by a second optical filter 48 which changes the wavelength of the light irradiating from the source 34 to a second wavelength, such as 325 nm. Both optical filters 36 and 48 may be contained in a holder 50 which is rotated or translated to position the desired one of the two filters in the optical path of the light source 34. The luminescence of the sample, after excitation at the second wavelength, is focused through a lens 52 and passes through a third optical filter before being detected by the photo-detector 46. The detected peak wavelength corresponds to hv3 in the examples described above.

Figure 13:
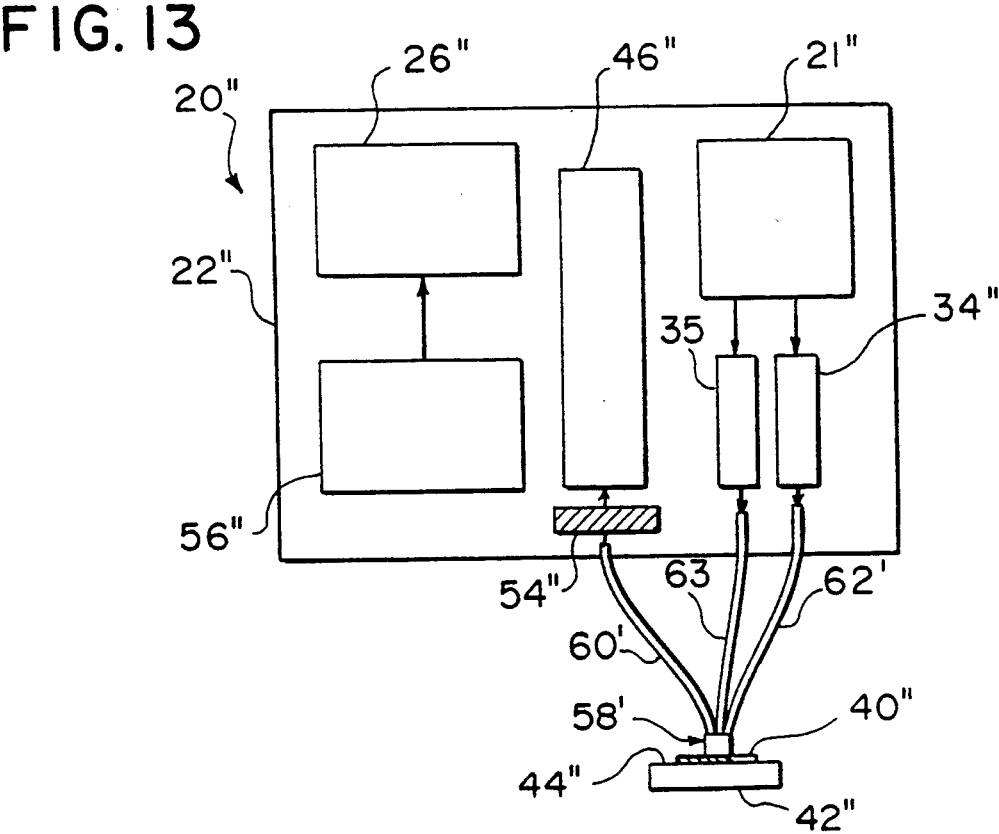
FIG. 13 is a schematic view of a variation of the portable field instrument of FIG. 12.

In another embodiment, illustrated in FIG. 13 and described more fully below, two different light sources are housed in the housing 22 and a mechanical shutter or electrical gating system allow photo-activation and excitation of the sample 40. The system can also be programmed to set and synchronize the photo-activation, excitation and detection cycles automatically.

An electrical signal indicative of the detected luminescence is delivered to a processor 56 which processes the photo-detector signal into an appropriate form. For example, the processor 56 could be programmed to output signals to the digital display 26 so as to give the operator either a reading of the spectra, the peak wavelength, or simply a "positive" or "negative" indication of PCB contained in the sample. Moreover, the processor 56 can be equipped with memory so that data can be gathered in the field and downloaded to a central computer for further analysis. Additional display devices can be provided on the portable instrument 20, including an X-Y plotter for providing a print-out of the detected spectra.

Figure 12:
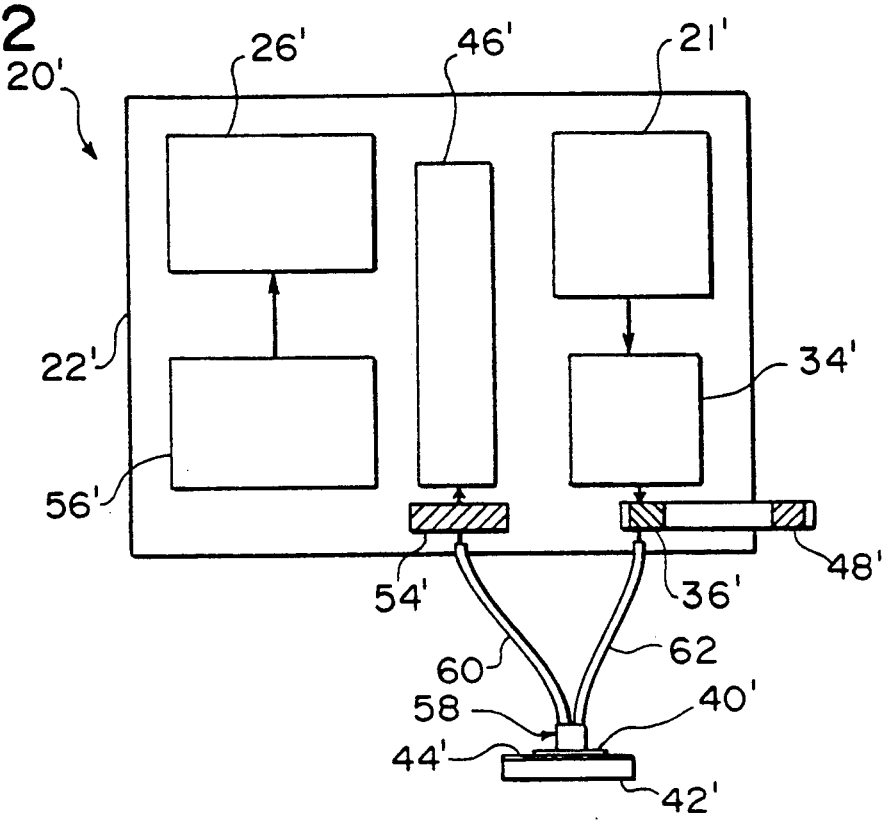
FIG. 12 is a schematic view of a variation of the portable field instrument of FIG. 10.

A variation of the embodiment of FIGS. 10 and 11 is seen in FIG. 12, in which like parts are of the same number, but primed, as in the prior embodiment. The difference lies in the fact that the sample holder 42' is external of the housing 22'. Samples 40' are screened by using a fiber optic probe 58 coupled to the housing 22' by two fiber optics 60 and 62. The fiber optic 62 delivers the UV light to the sample 40' after passing successively through filters 36' and 48'. Luminescence following the second excitation step is delivered through the fiber optic 60 to the photo-detector 46' after passing through the hv3 filter 54'.

In either embodiment, the use of two separate light sources, each having a different UV wavelength selected to accomplish the three-step method of the present invention can be used instead of a single source with two optical filters. In the interest of saving space, the single source with two optical filters is preferred. The hv1 filter 36, 36' provides photo-activation, and the hv2 filter 48, 48' provides excitation to a luminescence state. The hv3 filter 54, 54' is needed in either embodiment for luminescence detection. An example of two separate U.V. sources 34" and 35 is shown in FIG. 13 respectively optically coupled to fiber optics 62' and 63.

In order to improve the analysis, the present method can be combined with a rapid thin-layer chromatography (TLC) or paper chromatography (PC) separation that can be performed in situ on the sample substrate spotted with PCB samples. Since the present method involves luminescence on filter paper substrate, it is compatible with any chromatographic separations performed on the same substrate. This integrated procedure is simple, rapid and can improve the selectivity of the spot test since interfering compounds can be chromatographically separated from the PCBs. Also, different types of PCBs can also be chromatographically separated to a certain extent prior to luminescence detection.

Different types of Aroclors exhibit a maximum luminescence signal after different UV irradiation times. It is possible according to the present invention to use this difference in UV irradiation time in order to selectively increase the luminescence of a certain photo-product due to a certain type of Aroclors.

While advantageous embodiments have been chosen to illustrate the invention, it will be understood by those skilled in the art that various changes and modifications can be made therein without departing from the scope of the invention as defined in the appended claims.

What is claimed is:

1. An apparatus for testing a sample for the presence of PCBs and related organic chlorinated compounds, comprising:
   a photo-activator applied to the sample;
   first means for irradiating the sample with UV light of a first wavelength for a time sufficient to form a photo-product complex;
   second means for irradiating the photo-product complex with light of a second wavelength for a time sufficient to cause the photo-product to luminesce; and
   means for detecting the luminescence of the photo-product complex, the presence of PCBs and chlorinated compounds being determined by characteristics of the detected luminescence of the photo-product complex.

2. An apparatus according to claim 1, wherein the first and second means comprise a UV light source having an output irradiation beam, and first and second optical filters positionable selectively in an optical path of the irradiation beam.

3. An apparatus according to claim 2, wherein the first optical filter transmits the first wavelength of UV light at <254 nm and the second optical filter transmits the second wavelength of UV light at <360 nm and >254 nm.

4. An apparatus according to claim 3, wherein the detecting means includes a photo-detector and a third optical filter disposed between the sample and the photo-detector, the third optical filter transmitting a third wavelength of light to the photo-detector, the third wavelength corresponding to a peak wavelength of a luminescence spectrum detected by the photo-detector.

5. An apparatus according to claim 1, wherein the first and second means comprises first and second light sources.

6. An apparatus according to claim 1, further comprising a substrate for holding the sample in an optical path between the detecting means and the second means, said substrate being treated with a surfactant.

7. An apparatus according to claim 1, wherein the photo-activator is selected from the group consisting of indole, diphenylamine, pyrrole, and imidazole.

8. An apparatus according to claim 6, wherein the photo-activator is carried by the substrate.

9. An apparatus according to claim 6, wherein the surfactant is selected from the group consisting of sodium lauryl sulfate, CTAB, ethylene oxide, propylene oxide, cyclodextrin, and micellar.

10. An apparatus according to claim 1, further comprising a substrate for holding the sample in an optical path between the detecting means and the second means, said substrate being treated with a semiconductor particles.

11. An apparatus according to claim 9, wherein the semiconductor particles are TiO$_2$.

12. A portable field instrument for screening a sample for PCBs and related organic chlorinated compounds, comprising:
a photo-activator to be mixed with the sample prior to screening;
a housing;
a power source disposed within the housing;
a UV light source disposed within the housing and being powered by the power source;
a substrate positioned in an optical path of an irradiating output beam of the UV light source, and having the sample mountable thereon;
first and second optical filters selectively positionable in the optical path of the UV light source, each transmitting UV light at a different wavelength, the first filter transmitting UV light sufficient to photo-activate and form a photo-product complex of the photo-activator and chlorinated compounds, and the second optical filter transmitting UV light sufficient to cause the complex to luminesce; and
detecting means, disposed within the housing, for detecting the luminescence of the complex, the detected luminescence having a characteristic indicative of the presence or absence of chlorinated compounds.

13. An apparatus according to claim 12, wherein the detecting means includes a photo-detector and a third optical filter, both located inside the housing, and the third optical filter being disposed between the sample and the photo-detector, the third optical filter transmitting a third wavelength of the light to the photo-detector, the third wavelength corresponding to a peak wavelength of a luminescence spectrum detected by the photo-detector.

14. An apparatus according to claim 12, wherein the substrate is located within the housing.

15. An apparatus according to claim 12, wherein the substrate is located outside of the housing, and the apparatus further comprises a fiber optic probe having a first fiber optic for communicating UV light from the first and second optical filters to the sample, and a second fiber optic for communicating UV luminescent light from the sample to the detecting means.

* * * * *